US011219363B2

(12) United States Patent
Ono

(10) Patent No.: US 11,219,363 B2
(45) Date of Patent: Jan. 11, 2022

(54) OPHTHALMIC APPARATUS AND OPHTHALMIC OPTICAL COHERENCE TOMOGRAPHY METHOD

(71) Applicant: TOPCON CORPORATION, Tokyo (JP)

(72) Inventor: Yusuke Ono, Kita-ku (JP)

(73) Assignee: TOPCON CORPORATION, Tokyo (JP)

( * ) Notice: Subject to any disclaimer, the term of this patent is extended or adjusted under 35 U.S.C. 154(b) by 221 days.

(21) Appl. No.: 16/476,113

(22) PCT Filed: Dec. 8, 2017

(86) PCT No.: PCT/JP2017/044183
§ 371 (c)(1),
(2) Date: Jul. 5, 2019

(87) PCT Pub. No.: WO2018/135174
PCT Pub. Date: Jul. 26, 2018

(65) Prior Publication Data
US 2019/0350455 A1    Nov. 21, 2019

(30) Foreign Application Priority Data
Jan. 23, 2017    (JP) .............................. JP2017-009514

(51) Int. Cl.
*A61B 3/12*    (2006.01)
*A61B 3/00*    (2006.01)
(Continued)

(52) U.S. Cl.
CPC .............. *A61B 3/12* (2013.01); *A61B 3/0091* (2013.01); *A61B 3/102* (2013.01); *A61B 3/14* (2013.01)

(58) Field of Classification Search
CPC ......... A61B 3/12; A61B 3/0091; A61B 3/102; A61B 3/14
(Continued)

(56) References Cited

U.S. PATENT DOCUMENTS

2005/0046794 A1*   3/2005  Silvestrini .............. A61B 3/152
                                                         351/200
2011/0137157 A1    6/2011  Imamura et al.
(Continued)

FOREIGN PATENT DOCUMENTS

JP    2011-120656 A    6/2011
JP    2013-150696 A    8/2013
(Continued)

OTHER PUBLICATIONS

International Search Report and Written Opinion dated Feb. 27, 2018 for PCT/JP2017/044183 filed on Dec. 8, 2017, 8 pages including English Translation of the International Search Report.
(Continued)

*Primary Examiner* — Mohammed A Hasan
(74) *Attorney, Agent, or Firm* — Xsensus LLP

(57) ABSTRACT

An ophthalmic apparatus according to an embodiment includes a fixation system, a data acquisition device, analyzing circuitry, and controlling circuitry. The fixation system projects fixation light onto a subject's eye. The data acquisition device acquires data by applying optical coherence tomography scanning to the subject's eye onto which the fixation light is being projected. The analyzing circuitry analyzes the data to specify the position of a predetermined site of the subject's eye. The controlling circuitry controls at least one of the fixation system and the data acquisition device based on the positional relationship between the position of the predetermined site specified by the analyzing circuitry and a scan area by the data acquisition device.

11 Claims, 8 Drawing Sheets

(51) Int. Cl.
*A61B 3/10* (2006.01)
*A61B 3/14* (2006.01)

(58) Field of Classification Search
USPC .......................................................... 351/206
See application file for complete search history.

(56) References Cited

U.S. PATENT DOCUMENTS

| 2011/0170062 A1 | 7/2011 | Isogai et al. |
| 2012/0127428 A1 | 5/2012 | Isogai et al. |
| 2013/0188130 A1 | 7/2013 | Inoue |
| 2017/0273557 A1* | 9/2017 | Nakazawa ................ G06T 7/62 |

FOREIGN PATENT DOCUMENTS

| JP | 2015-128630 A | 7/2015 |
| JP | 5937163 B2 | 6/2016 |
| JP | 2016-158721 A | 9/2016 |

OTHER PUBLICATIONS

Extended European Search Report dated Jul. 20, 2020 in European Application No. 17893305.7.
Japanese Office Action dated Nov. 16, 2021 issued for the corresponding Japanese Patent Application No. 2017-009514.

* cited by examiner

OPHTHALMIC APPARATUS AND OPHTHALMIC OPTICAL COHERENCE TOMOGRAPHY METHOD

CROSS-REFERENCE TO RELATED APPLICATIONS

The present application is based on PCT filing PCT/JP2017/044183, filed Dec. 8, 2017 which claims priority to JP 2017-009514, filed Jan. 23, 2017, the entire contents of each are incorporated herein by reference.

FIELD

Embodiments described herein relate generally to an ophthalmic apparatus and ophthalmic optical coherence tomography method.

BACKGROUND

The ophthalmic apparatuses include ophthalmic imaging apparatuses for eye image acquisition, ophthalmic measurement apparatuses for ocular characteristic measurement and ophthalmic treatment apparatuses for eye treatment.

Examples of the ophthalmic imaging apparatuses include optical coherence tomography (OCT) scanners that acquire cross sectional images using OCT scanning, fundus cameras that capture fundus photographs, scanning laser ophthalmoscopes (SLOs) that acquire fundus images through laser scanning with confocal optical systems, slit lamp microscopes, and surgical microscopes.

Examples of the ophthalmic measurement apparatuses include eye refraction test devices (i.e., refractometers, keratometers) that measure refractive characteristics of eyes, tonometers, specular microscopes that acquire corneal characteristics (e.g., corneal thickness, cell distribution), wave front analyzers that acquire ocular aberration information with Hartmann-Shack sensors, and perimeters/microperimeters that measure visual fields.

Examples of the ophthalmic treatment apparatuses include laser treatment devices that project laser light onto treatment target sites such as diseased sites, surgical devices for specific purposes (e.g., cataract surgery, keratorefractive surgery), and surgical microscopes.

Many ophthalmic apparatuses have the function of presenting a fixation target to a subject's eye (or to its fellow eye). The fixation target has the function of guiding the line of sight to acquire data from a desired site of the eye and the function of fixing the eye during data acquisition.

PATENT DOCUMENT 1: Japanese Unexamined Patent Application Publication No. 2016-158721

SUMMARY

However, there are cases where the data of the desired site may not be acquired even if a fixation target is being presented. For example, the above functions of the fixation target may not be sufficiently exerted when the subject's eye has a visual acuity problem, or when the subject is an elderly person or a child. Also, the voluntary or involuntary movement of the subject's eye may interfere with fixation. Such phenomena are referred to as fixation loss.

A purpose of the present embodiment is to provide an ophthalmic apparatus capable of suitably dealing with fixation loss.

An ophthalmic apparatus of the first aspect of an embodiment includes a fixation system, a data acquisition device, analyzing circuitry, and controlling circuitry. The fixation system projects fixation light onto a subject's eye. The data acquisition device acquires data by applying optical coherence tomography scanning to the subject's eye onto which the fixation light is being projected. The analyzing circuitry analyzes the data to specify the position of a predetermined site of the subject's eye. The controlling circuitry controls at least one of the fixation system and the data acquisition device based on the positional relationship between the position of the predetermined site specified by the analyzing circuitry and a scan area by the data acquisition device.

According to the ophthalmic apparatus of the second aspect of the embodiment, the controlling circuitry controls the data acquisition device to change the scan area based on the positional relationship.

According to the ophthalmic apparatus of the third aspect of the embodiment, the controlling circuitry controls the fixation system to change a fixation position based on the positional relationship.

According to the ophthalmic apparatus of the fourth aspect of the embodiment, the data acquisition device acquires an image of the subject's eye. The analyzing circuitry includes segmentation processing circuitry, position specifying circuitry, and positional relationship acquiring circuitry. The segmentation processing circuitry analyzes the image to specify at least one segment of the image. The position specifying circuitry specifies the position of the predetermined site based on the at least one segment. The positional relationship acquiring circuitry determines the positional relationship between the position of the predetermined site specified by the position specifying circuitry and the scan area by the data acquisition device. The controlling circuitry executes control for at least one of the fixation system and the data acquisition device based on the positional relationship determined by the positional relationship acquiring circuitry.

According to the ophthalmic apparatus of the fifth aspect of the embodiment, the segmentation processing circuitry specifies at least the first segment and the second segment of the image. The position specifying circuitry specifies the position of the predetermined site based on a distance distribution between the first segment and the second segment.

According to the ophthalmic apparatus of the sixth aspect of the embodiment, the data acquisition device acquires an image of the fundus of the subject's eye. The segmentation processing circuitry specifies an inner limiting membrane image as the first segment and specifies a Bruch membrane image as the second segment. The position specifying circuitry specifies the position at which the distance between the inner limiting membrane image and the Bruch membrane image is the shortest as the position of the macular center.

According to the ophthalmic apparatus of the seventh aspect of the embodiment, the data acquisition device acquires a three dimensional image by scanning a three dimensional region of the subject's eye. The analyzing circuitry analyzes the three dimensional image to specify the position of the predetermined site. The ophthalmic apparatus further includes image projecting circuitry, a photographing device, and registration processing circuitry. The image projecting circuitry constructs a front projection image from the three dimensional image. The photographing device photographs the subject's eye to acquire a front image. The registration processing circuitry performs registration between the front projection image and the front image. The controlling circuitry displays the front image on a display device and displays, based on the result of the registration, the first image based on the position of the predetermined site over the front image.

According to the ophthalmic apparatus of the eighth aspect of the embodiment, the controlling circuitry displays the second image indicating the scan area by the data acquisition device over the front image.

According to the ophthalmic apparatus of the ninth aspect of the embodiment, the controlling circuitry displays the front projection image over the front image.

According to the ophthalmic apparatus of the tenth aspect of the embodiment, the controlling circuitry compares a deviation of the scan area with respect to the position of the predetermined site with a predetermined threshold, and executes control for at least one of the fixation system and the data acquisition device only when the deviation exceeds the predetermined threshold.

According to the embodiment configured as described above, fixation loss can be treated in a suitable way.

DETAILED DESCRIPTION

Figure 1:
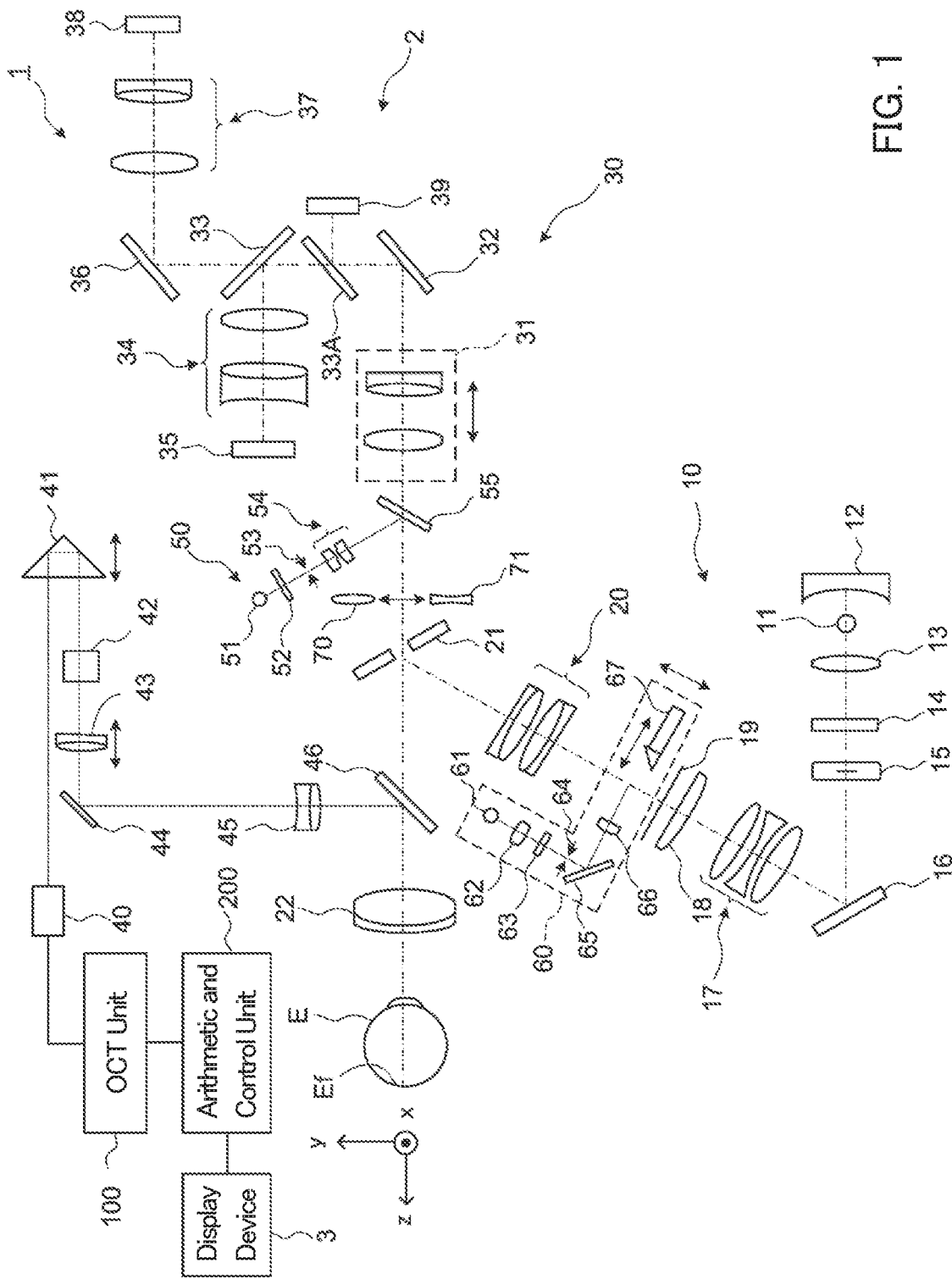
FIG. 1 is a schematic diagram illustrating an example of the configuration of an ophthalmic apparatus according to an embodiment.

Embodiment examples of the present invention will be described in detail with referring to the drawings. The ophthalmic apparatus according to the embodiment at least includes an OCT scanner.

In addition to the OCT scanner, the ophthalmic apparatus according to the embodiment may include any one or more of an ophthalmic imaging apparatus other than OCT scanners, an ophthalmic measurement apparatus, and an ophthalmic treatment apparatus. The ophthalmic imaging apparatus included in the ophthalmic apparatus according to the embodiment may be, for example, any one or more of a fundus camera, a scanning laser ophthalmoscope, a slit lamp microscope, and a surgical microscope. The ophthalmic measurement apparatus included in the ophthalmic apparatus according to the embodiment may be, for example, any one or more of an eye refraction test device, a tonometer, a specular microscope, a wave front analyzer, a perimeter, and a microperimeter. In addition, the ophthalmic treatment apparatus included in the ophthalmic apparatus according to the embodiment may be, for example, any one or more of a laser treatment device (photocoagulator), a surgical device, and a surgical microscope.

The ophthalmic apparatus according to the embodiment example described below includes an OCT scanner and a fundus camera. Swept source OCT is adopted to the OCT scanner in the embodiment example, however the type of OCT is not limited to this, and other OCT types (e.g., spectral domain OCT, time domain OCT, en-face OCT) may be adopted to other embodiment examples.

<Configuration>

As shown in FIG. 1, the ophthalmic apparatus 1 includes the fundus camera unit 2, the OCT unit 100 and the arithmetic and control unit 200. The fundus camera unit 2 is provided with optical systems and mechanisms for acquiring front images of the subject's eye E. The OCT unit 100 includes part of optical systems and part of mechanisms for performing OCT scanning. Another part of the optical systems and another part of the mechanisms for performing OCT scanning are provided in the fundus camera unit 2. The arithmetic and control unit 200 includes one or more processors that execute various calculations and controls. In addition to these, the ophthalmic apparatus 1 may also include any elements and/or units such as a member for supporting the subject's face (e.g., a chin rest, a forehead rest) and a lens unit for switching the sites subjected to OCT scanning. The lens unit is, for example, an attachment for anterior eye segment OCT scanning.

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a memory circuit or a memory device.

<Fundus Camera Unit 2>

The fundus camera unit 2 is provided with an optical system for photographing the fundus Ef of the subject's eye E. Images of fundus Ef (referred to as fundus images, fundus photographs, or the like) obtained include front images such as observation images and photographed images. An observation image is obtained by capturing a moving image using near-infrared light. A photographed image is a still image obtained by using flash light. Further, the fundus camera unit 2 is capable of capturing front images (anterior eye segment images) by photographing the anterior eye segment of the subject's eye E.

The fundus camera unit 2 includes the illumination optical system 10 and the photographing optical system 30. The illumination optical system 10 projects illumination light onto the subject's eye E. The photographing optical system 30 detects the return light of the illumination light from the subject's eye E. The measurement light incident from the OCT unit 100 is directed to the subject's eye E through the optical path in the fundus camera unit 2, and the return light thereof is directed to the OCT unit 100 through the same optical path.

The light output from the observation light source 11 of the illumination optical system 10 (referred to as observation illumination light) is reflected by the reflection mirror 12 having a curved reflective surface, passes through the condenser lens 13, and becomes near-infrared light after passing through the visible cut filter 14. Further, the observation illumination light is once converged near the photographing light source 15, reflected by the mirror 16, and passes through the relay lenses 17 and 18, the diaphragm 19, and the relay lens 20. Then, the observation illumination light is reflected on the peripheral part (i.e., the surrounding area of the aperture part) of the aperture mirror 21, penetrates the dichroic mirror 46, and is refracted by the objective lens 22, thereby illuminating the subject's eye E (the fundus Ef or the anterior eye segment thereof). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the return light passes through the half mirror 33A, is reflected by the dichroic mirror 33, and forms an image on the light receiving surface of the image sensor 35 by the condenser lens 34. The image sensor 35 detects the return light at a predetermined frame rate. Note that the focus of the photographing optical system 30 is regulated to coincide with the fundus Ef or the anterior eye segment.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to the dichroic mirror 33, passes through the dichroic mirror 33, is reflected by the mirror 36, and forms an image on the light receiving surface of the image sensor 38 by the condenser lens 37.

The liquid crystal display (LCD) 39 displays a fixation target and a visual acuity measurement target. Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

The fixation position of the subject's eye E can be changed by changing the display position of the fixation target on the screen of the LCD 39. Examples of the fixation position include the followings: a fixation position for acquiring an image centered on the macula; a fixation position for acquiring an image centered on the optic nerve head; a fixation position for acquiring an image centered on the fundus center that is located between the macula and the optic nerve head; and a fixation position for acquiring an image of a site far away from the macula (periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, capable of changing the fixation position, to the subject's eye E is not limited to display devices such as an LCD. For example, the fixation target that is capable of changing the fixation position can be generated by lighting one (or more) of the plurality of light sources in a light source array (e.g., a light emitting diode (LED) array) in a selective manner. Optionally, the fixation target that is capable of changing the fixation position can be generated by employing one or more movable light sources.

The alignment optical system 50 generates an alignment indicator used for the alignment of the optical system with respect to the subject's eye E. The alignment light output from the LED 51 travels through the diaphragm 52, the diaphragm 53, and the relay lens 54, is reflected by the dichroic mirror 55, and passes through the aperture part of the aperture mirror 21. The light having passed through the aperture part of the aperture mirror 21 penetrates the dichroic mirror 46, and is projected onto the subject's eye E via the objective lens 22. The cornea reflection light of the alignment light passes through the same route as that of the return light of the observation illumination light and is guided to the image sensor 35. Based on the received image (referred to as the alignment indicator image), manual alignment and/or automatic alignment can be performed.

The focus optical system 60 generates a split indicator used for the focus adjustment with respect to subject's eye E. In conjunction with the movement of the photography focusing lens 31 along the optical path of the photographing optical system 30 (referred to as the photographing optical path), the focus optical system 60 is moved along the optical path of the illumination optical system 10 (referred to as the illumination optical path). The reflection rod 67 can be inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64, is reflected by the mirror 65, and is converged on the reflective surface of the reflection rod 67 by the condenser lens 66. Further, the focus light travels through the relay lens 20, is reflected by the aperture mirror 21, and penetrates the dichroic mirror 46, thereby being projected onto the subject's eye E via the objective lens 22. The fundus reflection light of the focus light passes through the same route as the cornea reflection light of the alignment light and is guided to the image sensor 35. Based on the image (referred to as the split indicator image), manual focusing and/or automatic focusing can be performed.

The diopter correction lenses 70 and 71 can be selectively inserted into the position in the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT scanning together. The dichroic mirror 46 reflects the light of wavelength bands used for OCT scanning and transmits the light for fundus photography. Listed from the OCT unit 100 side to the dichroic mirror 46 side, the collimator lens unit 40, the optical path length changing device (OPL changing device) 41, the optical scanner 42, the OCT focusing lens 43, the mirror 44, and the relay lens 45 are arranged in the OCT optical path (the optical path of the measurement light).

The OPL changing device 41 is movable in the directions indicated by the arrow in FIG. 1, whereby the length of the OCT optical path is changed. The change in the optical path length can be utilized for correcting the optical path length according to the axial length, and for regulating the interference condition, for example. The OPL changing device 41 includes a corner cube and a mechanism for moving the corner cube.

The optical scanner 42 is placed at a position optically conjugate with the pupil of the subject's eye E. The optical scanner 42 deflects the measurement light LS passing through the OCT optical path. The optical scanner 42 is, for example, a Galvano mirror scanner capable of two dimensional scanning.

The OCT focusing lens 43 is moved along the optical path of the measurement light LS in order to perform the focus adjustment of the optical system for OCT. The movement of the photography focusing lens 31, the movement of the focus optical system 60, and the movement of the OCT focusing lens 43 can be controlled in an interlocking manner.

<OCT Unit 100>

Figure 2:
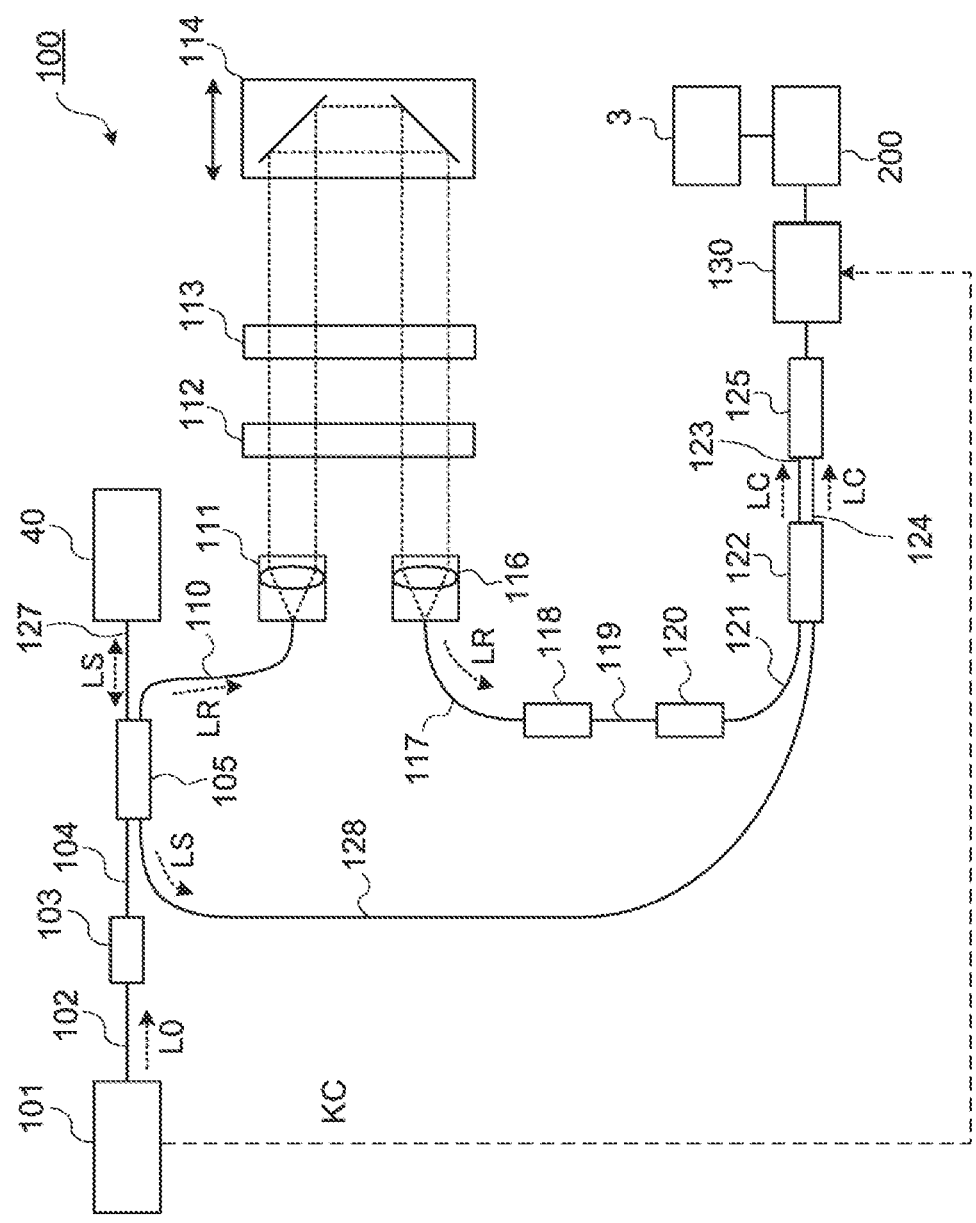
FIG. 2 is a schematic diagram illustrating an example of the configuration of the ophthalmic apparatus according to the embodiment.

As illustrated in FIG. 2, the OCT unit 100 is provided with the optical system for performing swept source OCT. The optical system includes an interference optical system. The interference optical system has the function of splitting the light emitted from the light source of wavelength tunable type (also referred to as wavelength swept type) into measurement light and reference light, the function of superposing the return light of the measurement light from the subject's eye E and the reference light having traveled through the reference optical path to generate interference light, and the function of detecting the interference light. The result of the detection (i.e., detection signal) of the interference light obtained by the interference optical system is a signal representing a spectrum of the interference light. The detection signal is sent to the arithmetic and control unit 200.

The light source unit 101 includes, for example, a near infrared tunable laser configured to change the wavelengths of emitted light at high speed. The light LO output from the light source unit 101 is guided to the polarization controller 103 through the optical fiber 102, and the polarization state of the light LO is regulated. Further, the light LO is guided to the fiber coupler 105 through the optical fiber 104 and is split into the measurement light LS and the reference light LR.

The reference light LR is guided through the optical fiber 110 to the collimator 111, is converted into a parallel light beam, travels through the optical path length correction member 112 and the dispersion compensation member 113, and is guided to the corner cube 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other. The corner cube 114 is movable in the incident direction of the reference light LR, whereby the optical path length of the reference light LR is changed.

The reference light LR that has passed through the corner cube 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the OPL changing device 41, the optical scanner 42, the OCT focusing lens 43, the mirror 44, and the relay lens 45, and then reaches the dichroic mirror 46. The measurement light LS is reflected by the dichroic mirror 46, is refracted by the objective lens 22, and is incident on the subject's eye E. The measurement light LS is reflected and scattered at various depth positions of the subject's eye E. The return light of the measurement light LS from the subject's eye E travels along the same route as the outward way in the opposite direction, is directed to the fiber coupler 105, and then reaches the fiber coupler 122 via the optical fiber 128.

The fiber coupler 122 couples (superposes) the measurement light LS incident through the optical fiber 128 and the reference light LR incident through the optical fiber 121, to generate interference light. The fiber coupler 122 splits the interference light at a predetermined splitting ratio (e.g., 1:1) to generate a pair of interference light LC. The pair of the interference light LC is guided to the detector 125 through the optical fibers 123 and 124, respectively.

The detector 125 is, for example, a balanced photodiode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the DAQ 130. The clock KC is generated in the light source unit 101 in synchronization with the output timings of the respective wavelengths varied within a predetermined wavelength range by the wavelength tunable type light source. For example, the light source unit 101 splits the light LO of each output wavelength to generate two pieces of split light, optically delays one of the two pieces of split light, generates the combined light of the two pieces of split light, and generates the clock KC based on the result of the detection of the combined light. The DAQ 130 performs the sampling of the detection signal input from the detector 125 based on the clock KC. The DAQ 130 sends the result of the sampling of the detection signal from the detector 125 to the arithmetic and control unit 200.

The present example is provided with both the OPL changing device 41 for changing the length of the optical path of the measurement light LS (referred to as the measurement optical path or the measurement arm) and the corner cube 114 for changing the length of the optical path of the reference light LR (referred to as the reference optical path or the reference arm). However, only one of the OPL changing device 41 and the corner cube 114 may be provided. Another optical element may be employed to change the difference between the measurement optical path length and the reference optical path length.

<Control System>

Figure 3A:
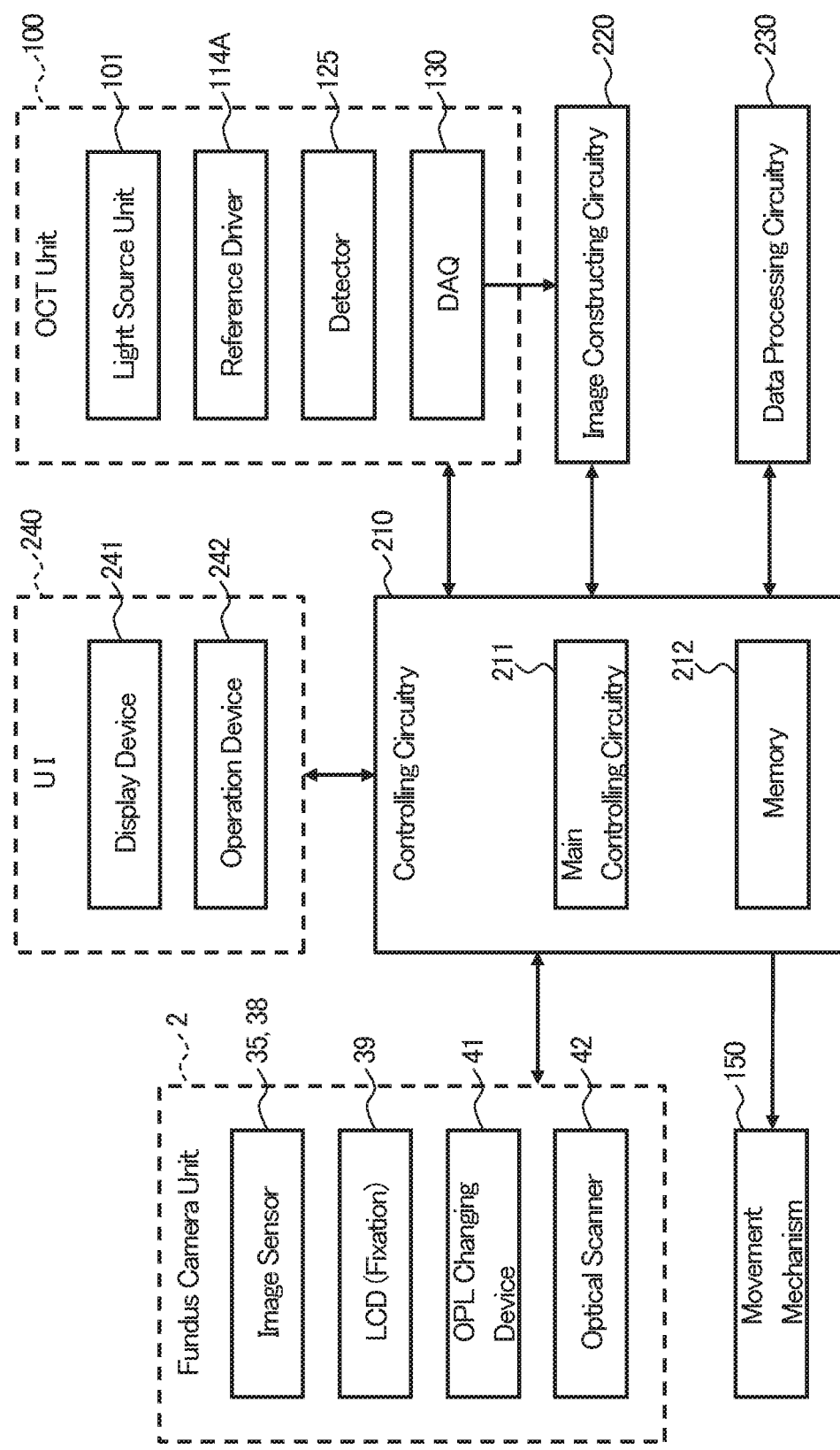
FIG. 3A is a schematic diagram illustrating an example of the configuration of the ophthalmic apparatus according to the embodiment.
Figure 3B:
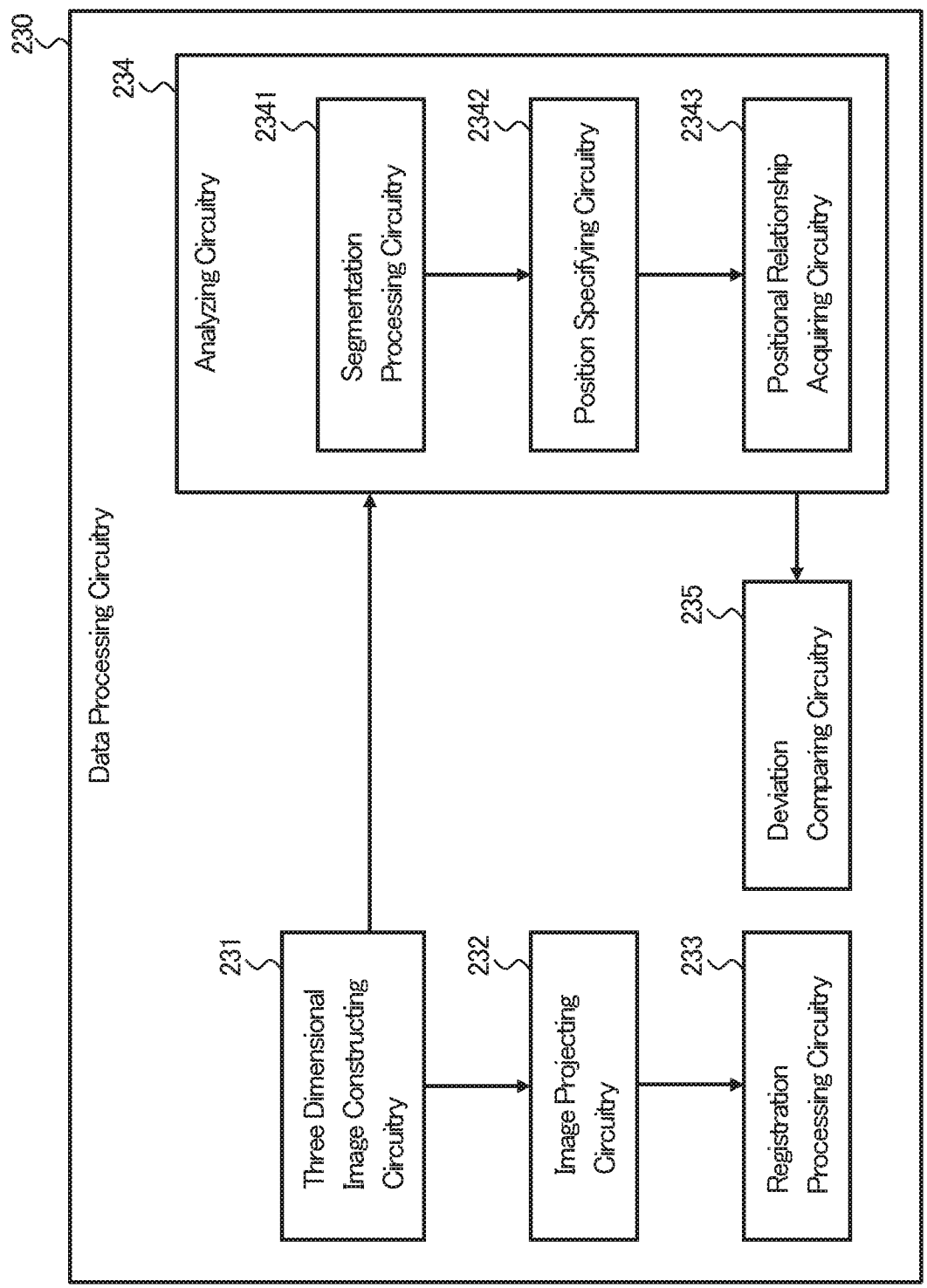
FIG. 3B is a schematic diagram illustrating an example of the configuration of the ophthalmic apparatus according to the embodiment.

FIG. 3A and FIG. 3B show examples of the configuration of the control system of the ophthalmic apparatus 1. FIG. 3A and FIG. 3B omit some of the components included in the ophthalmic apparatus 1. The controlling circuitry 210, the image constructing circuitry 220 and the data processing circuitry 230 are provided, for example, in the arithmetic and control unit 200.

<Controlling Circuitry 210>

The controlling circuitry 210 performs various kinds of controls. The controlling circuitry 210 includes the main controlling circuitry 211 and the memory 212.

<Main Controlling Circuitry 211>

The main controlling circuitry 211 includes a processor(s), and controls each part of the ophthalmic apparatus 1 (including each component shown in FIG. 1 to FIG. 3B). For example, the main controlling circuitry 211 moves the photography focusing lens 31 by controlling a driving mechanism (not shown in figures). Further, the main controlling circuitry 211 moves the OCT focusing lens 43 by controlling a driving mechanism (not shown in figures). In addition, the main controlling circuitry 211 moves the corner cube 114 by controlling the reference driver 114A.

The movement mechanism 150 moves, for example, at least the fundus camera unit 2 in a three dimensional manner. In a typical example, the movement mechanism 150 includes the followings: a mechanism for moving at least the fundus camera unit 2 in the x direction (i.e., left and right direction); a mechanism for moving at least the fundus camera unit 2 in the y direction (i.e., up and down direction); and a mechanism for moving at least the fundus camera unit 2 in the z direction (i.e., depth direction, front and back direction). The mechanism for moving at least the fundus camera unit 2 in the x direction includes, for example, an x stage movable in the x direction and an x movement mechanism that moves the x stage. The mechanism for moving at least the fundus camera unit 2 in the y direction includes, for example, a y stage movable in the y direction and a y movement mechanism that moves the y stage. The mechanism for moving at least the fundus camera unit 2 in the z direction includes, for example, a z stage movable in the z direction and a z movement mechanism that moves the z stage. Each of the movement mechanisms includes an actuator such as a pulse motor and operates under the control of the main controlling circuitry 211.

The main controlling circuitry 211 controls the LCD 39. For example, the main controlling circuitry 211 displays a fixation target at a position on the screen of the LCD 39 corresponding to the manually or automatically set fixation position. Further, the main controlling circuitry 211 can change (in a continuous or stepwise manner) the display position of the fixation target displayed on the LCD 39, whereby the fixation target can be moved (i.e., the fixation position can be changed). The display position and movement mode of the fixation target are set manually or automatically. The manual setting is performed using a GUI, for example. The automatic setting is performed by the data processing circuitry 230, for example.

<Memory 212>

The memory 212 stores various kinds of data. Examples of the data stored in the memory 212 includes OCT images, fundus images, anterior eye segment images, and subject's eye information. The subject's eye information includes subject information such as the patient ID and the patient's name, identification information for the left eye and the right eye, and electronic medical record information.

<Image Constructing Circuitry 220>

The image constructing circuitry 220 includes a processor, and constructs an image based on the output from the DAQ 130 (that is, based on the result of the detection signal sampling). For example, as in the conventional swept source OCT, the image constructing circuitry 220 applies signal processing to the spectral distribution formed from the sampling result for each A-line to form the reflection intensity profile for each A-line. Then, the image constructing circuitry 220 creates a plurality of pieces of image data from the reflection intensity profiles for a plurality of A-lines and arranges the plurality of pieces of image data along a scan line(s). The aforementioned signal processing includes noise elimination (or noise reduction), filtering, and fast Fourier transform (FFT), for example.

<Data Processing Circuitry 230>

The data processing circuitry 230 includes a processor, and applies image processing and/or analysis to the image constructed by the image constructing circuitry 220. The data processing circuitry 230 includes the three dimensional image constructing circuitry 231, the image projecting circuitry 232, the registration processing circuitry 233, the analyzing circuitry 234, and the deviation comparing circuitry 235.

<Three Dimensional Image Constructing Circuitry 231>

The three dimensional image constructing circuitry 231 operates when OCT scanning has been performed on a three dimensional region of the subject's eye E (in other words, when OCT scanning has been performed for acquiring a three dimensional image).

When OCT scanning of a three dimensional region has not been performed, the processing by the analyzing circuitry 234, etc. is performed without the processing by the three dimensional image constructing circuitry 231. Note that the image projecting circuitry 232 and the registration processing circuitry 233 also operate after OCT scanning of a three dimensional region of the subject's eye E has been performed.

Examples of scan modes (i.e., scan patterns) for three dimensional region scanning include raster scan (three dimensional scan), radial scan, and multi-cross scan. The raster scan is a mode of scanning a plurality of lines parallel to each other in a sequential manner. The radial scan is a mode of scanning a plurality of radially arranged lines in a sequential manner. The multi-cross scan is a mode of scanning a first line group consisting of a predetermined number of lines parallel to each other and a second line group consisting of a predetermined number of lines orthogonal to the first line group in a sequential manner.

The types of three dimensional image constructed by the three dimensional image constructing circuitry 231 is arbitrary. A three dimensional image typically means an image in which the pixel positions are defined using a three dimensional coordinate system. In an embodiment example, three dimensional image constructing circuitry 231 constructs stack data or volume data as three dimensional images.

Stack data is constructed by embedding a plurality of cross sectional images (B-scan images, for example, xz cross sectional images) constructed by the image constructing circuitry 220 based on data acquired by three dimensional region scanning, into a single three dimensional coordinate system (that is, into a single three dimensional space). In other words, stack data is obtained by arranging a plurality of B-scan images obtained along a plurality of scan lines in a three dimensional manner, based on the positional relationship of the scan lines.

Volume data is constructed by interpolation and voxelization of pixels between a plurality of B-scan images included in stack data. Volume data is also referred to as voxel data.

When displaying the three dimensional image constructed in this way, the data processing circuitry 230 can perform rendering. Examples of the rendering include volume rendering and maximum intensity projection (MIP).

The data processing circuitry 230 can construct a two dimensional cross sectional image from the three dimensional image. Multi-planar reconstruction (MPR) is an example of this process.

<Image Projecting Circuitry 232>

The image projecting circuitry 232 constructs front projection images from the three dimensional images constructed by the three dimensional image constructing circuitry 231. A front projection image is a two dimensional image constructed by projecting a three dimensional image in a predetermined direction. The three dimensional image projection processing includes a process of adding the values of a plurality of pixels arranged along the predetermined direction.

Projection images and shadowgrams are typical examples of front projection images. A projection image is constructed by projecting a three dimensional image in a predetermined direction (i.e., the z direction, depth direction, A-scan direction). As with fundus images obtained by the fundus camera unit 2, the surface morphology (surface appearance) of the fundus Ef is represented in a front projection image constructed from a three dimensional image of the fundus Ef.

A shadowgram is constructed by projecting part of a three dimensional image (e.g., partial data corresponding to a specific layer) in a predetermined direction. Projecting partial data including the surface tissue of the fundus Ef (e.g., the inner limiting membrane and layers in the vicinity thereof) yields a front projection image in which the surface morphology of the fundus Ef is represented like fundus images.

<Registration Processing Circuitry 233>

The registration processing circuitry 233 performs registration between the fundus image obtained by the fundus camera unit 2 and the front projection image constructed by the image projecting circuitry 232.

When an observation image is obtained by the fundus camera unit 2, the registration processing circuitry 233 can perform registration for each of the image frames sequentially acquired as the observation image. Alternatively, registration may be performed at a predetermined frame interval.

When a series of OCT scans (e.g., raster scan) is performed in an iterative manner, the image constructing circuitry 220 and the three dimensional image constructing circuitry 231 construct three dimensional images from a series of data acquired in each of the series of OCT scans performed in a sequential manner. More specifically, the image constructing circuitry 220 and the three dimensional image constructing circuitry 231 iteratively perform processing for constructing three dimensional images in synchronization with the iteration of the series of OCT scans. Further, the image projecting circuitry 232 can construct a front projection image from each of the sequentially constructed three dimensional images. The registration processing circuitry 233 can apply registration to each of the front projection images sequentially constructed.

In the case where an observation image is obtained by the fundus camera unit 2 and a series of OCT scans is iteratively performed, the registration processing circuitry 233 can pair an image frame of the observation image and a front projection image based on the frame rate of the observation image and the iteration rate (repetition rate) of the series of OCT scans, and then apply registration to each of the pairs. At this time, the main controlling circuitry 211 can synchronize the acquisition timings of the image frames of the observation image and the iteration timings of the series of OCT scans with each other.

The registration includes, for example, the followings: the first process of detecting feature regions from the both images (i.e., the fundus image and the front projection image); and the second process of applying registration to the both images with the both feature regions as references.

The feature regions detected in the first process may be, for example, any of the followings: a region corresponding to the optic nerve head; a region corresponding to the macula; a region corresponding to a feature blood vessel; a region corresponding to a lesioned part; and a region corresponding to a laser treatment scar. In the first process, the registration processing circuitry 233 can detect feature regions with reference to the pixel values and the pixel arrangements.

In the second process, the registration processing circuitry 233 adjusts the relative position between the fundus image and the front projection image to match the feature region detected from the fundus image and the feature region detected from the front projection image with one another, for example. At this time, the registration processing circuitry 233 may specify the contours or representative points (e.g., the center point, the center of gravity) of the feature region and perform registration to coincide the both contours or the both representative points with one another. In addition, the registration processing circuitry 233 may evaluate the degree of coincidence of the both feature regions, and determine that the both feature regions coincide with one another if the calculated evaluation value is equal to or greater than a predetermined threshold.

<Analyzing Circuitry 234>

The analyzing circuitry 234 analyzes the data acquired by OCT scanning to specify the position of a predetermined site of the subject's eye E.

Here, the predetermined site of the subject's eye E may be any site. For example, when OCT scanning is performed on the fundus Ef, the predetermined site may be the macula, the optic nerve head, a lesioned part, an interested blood vessel, etc. Alternatively, when OCT scanning is performed on the anterior eye segment, the predetermined site may be the corner angle, the ciliary body, etc.

Further, the position of the predetermined site specified by the analyzing circuitry 234 may be, for example, a position in the data acquired by the OCT scanning (i.e., a position in the scan area).

The analyzing circuitry 234 includes the segmentation processing circuitry 2341, the position specifying circuitry 2342, and the positional relationship acquiring circuitry 2343.

In the present embodiment, a three dimensional image constructed by the three dimensional image constructing circuitry 231 is input to the analyzing circuitry 234. Alternatively, when OCT scanning is not performed on an three dimensional region of the subject's eye E, an image constructed by the image constructing circuitry 220 (or an image created by processing the image constructed by the image constructing circuitry 220 by the data processing circuitry 230, etc.) is input into the analyzing circuitry 234.

Hereinafter, a case of processing a three dimensional image will be described in particular. However, similar processing can be performed also in a case where other images have been obtained.

<Segmentation Processing Circuitry 2341>

The segmentation processing circuitry 2341 analyzes the three dimensional image to specify at least one segment of the three dimensional image. The segment specified is typically an image of a layer tissue of eye, or an image of a layer boundary.

Examples of the segment specified from the three dimensional image of the fundus Ef include, an image of the inner limiting membrane, an image of the nerve fiber layer, an image of the ganglion cell layer, an image of the inner plexiform layer, an image of the inner nuclear layer, an image of the outer plexiform layer, an image of the outer nuclear layer, an image of the external limiting membrane, an image of the retinal pigment epithelium, an image of the Bruch membrane, an image of the choroid, an image of the choroid-sclera interface, and an image of the sclera.

In a typical embodiment example, the segmentation processing circuitry 2341 specifies two segments. For example, when the predetermined site of the subject's eye E whose position is specified by the analyzing circuitry 234 is the macular center (i.e., fovea centralis), the segmentation processing circuitry 2341 may be configured to specify the inner limiting membrane image and the Bruch membrane image. Of course, the configuration of the segmentation processing circuitry 2341 is not limited to this.

The segmentation processing circuitry 2341 can perform segmentation based on changes in the pixel values of the three dimensional image, as in a conventional case. For example, the segmentation processing circuitry 2341 may be configured to specify a feature value from among the values of the pixel group arranged in each A-line, and select a pixel(s) having the specified value to be a pixel(s) constituting the target segment.

The segmentation processing circuitry 2341 may be configured to determine an approximate curve of the boundary of two adjacent layers. The approximate curve can be determined with any method. Examples of the approximate curve include a linear approximate curve, a logarithmic approximate curve, a polynomial approximate curve, a power approximate curve, an exponential approximate curve, and a moving average approximate curve.

<Position Specifying Circuitry 2342>

The position specifying circuitry 2342 specifies the position of the predetermined site of the subject's eye E based on the at least one segment specified by the segmentation processing circuitry 2341.

When the segmentation processing circuitry 2341 has specified a single segment, for example, the position specifying circuitry 2342 can specify the position of the predetermined site of the subject's eye E based on any information on the segment such as its position, size, shape, etc. Sites specifiable (detectable) with such processing are the optic nerve head, the macula (macular center), lesioned parts, etc.

When the segmentation processing circuitry 2341 has specified two (or more) segments, for example, the position specifying circuitry 2342 can specify the position of the predetermined site of the subject's eye E based on any information on these segments such as their positions, relative positions, sizes, relative sizes, shapes, relative shapes, etc. Sites specifiable (detectable) with such processing are the optic nerve head, the macula (macular center), and lesioned parts, etc.

In a typical example, the segmentation processing circuitry 2341 can specify the first segment and the second segment. In this case, the position specifying circuitry 2342 can specify the position of the predetermined site based on the distribution of the distance between the first segment and the second segment.

A specific example will be described. When a three dimensional image of the fundus Ef is acquired, the segmentation processing circuitry 2341 specifies the inner limiting membrane image and the Bruch membrane image. The position specifying circuitry 2342 determines the distribution of the distance between the inner limiting membrane image and the Bruch membrane image. The distance distribution represents the distribution of the thicknesses of the layer existing between the inner limiting membrane and the Bruch membrane (i.e., retinal thickness distribution).

In general, the macula is detected as a depression in the inner limiting membrane in the direction towards the Bruch membrane. Further, the macular center is generally detected as the deepest position in the depression. In consideration of such anatomical features, the position specifying circuitry 2342 can search for a position having the shortest distance in the distance distribution between the inner limiting membrane image and the Bruch membrane image. Then, the position specifying circuitry 2342 can set the searched position to be the macular center position.

There are cases where two or more positions corresponding to the shortest distance are searched from the distance distribution. In such cases, the position specifying circuitry 2342 can determine whether or not each of the searched positions corresponds to the macular center position, based on, for example, neighborhood distance distribution around that position. Alternatively, the position specifying circuitry 2342 can determine whether or not each of the searched positions corresponds to the macular center position, based on the shape (e.g., depression shape) of the inner limiting membrane image in the neighborhood region around that position. More generally, the position specifying circuitry 2342 can specify the position of the predetermined site of the fundus Ef based on information including at least the above-described distance distribution.

<Positional Relationship Acquiring Circuitry 2343>

The positional relationship acquiring circuitry 2343 determines the positional relationship between the position of the predetermined site of the subject's eye E specified by the position specifying circuitry 2342 and the area to which OCT scanning is applied (referred to as a scan area).

In a typical example, the positional relationship acquiring circuitry 2343 can determine the deviation of the scan area with respect to the position of the predetermined site of the subject's eye E. Here, the deviation of the scan area with respect to the position of the predetermined site of the subject's eye E is substantially equal to the deviation of the position of the predetermined site of the subject's eye E with respect to the scan area.

For example, the positional relationship acquiring circuitry 2343 can determine the difference (e.g., the deviation vector) between the position of the predetermined site of the subject's eye E and a preset position in the scan area. More specifically, the positional relationship acquiring circuitry 2343 determines any one of the followings: the deviation vector whose initial point is placed at the position of the predetermined site of the subject's eye E and whose terminal point is placed at the preset position in the scan area; and the deviation vector whose initial point is placed at the preset position in the scan area and whose terminal point is placed at the position of the predetermined site of the subject's eye E.

The preset position in the scan area may be set in an arbitrary manner. For example, the preset position in the scan area is set to any of the center of the scan area, the position in which a plurality of scan lines intersect, and a position on the outer edge of the scan area (e.g., apex position, middle point position of a side, etc.).

The preset position in the scan area may be a region having a certain size. For example, a certain region containing the center of the scan area may be set as the preset position. Alternatively, the outer edge of the scan area may be set as the preset position.

In such cases, the positional relationship acquiring circuitry 2343 may be configured to determine, for example, a deviation vector that is oriented along the shortest distance line between the position of the predetermined site of the subject's eye E and the certain region in the scan area. In another example, the positional relationship acquiring circuitry 2343 may be configured to determine a deviation vector that connects the position of the predetermined site of the subject's eye E and a representative position (e.g., the center, the center of gravity, a position on the outer edge, etc.) in the certain region.

Similarly, the position of the predetermined site of the subject's eye E may be a region having a certain size. For example, the positional relationship acquiring circuitry 2343 may be configured to determine a deviation vector based on a region whose center is the position specified by the position specifying circuitry 2342 (e.g., a circular region, a rectangular region, etc.) and a preset position in the scan area. The size of that region is determined by, for example, the imaging magnification, the size of the scan area, etc.

Both the preset position in the scan area and the position of the predetermined site of the subject's eye E may be regions of certain sizes. In such cases, the positional relationship acquiring circuitry 2343 can determine the positional relationship between the both regions.

For example, the positional relationship acquiring circuitry 2343 can determine whether or not the region of the predetermined site of the subject's eye E (e.g., the macular center and the vicinity thereof) is contained inside the outer edge of the scan area. This determination is, for example, substantially the same processing as the determination regarding the magnitude of the difference between the position of the predetermined site of the subject's eye E (e.g., the macular center) and the center of the scan area.

<Deviation Comparing Circuitry 235>

The deviation comparing circuitry 235 compares the deviation determined by the positional relationship acquiring circuitry 2343 with a predetermined threshold. This deviation is, for example, the magnitude of the deviation vector described above. The deviation comparing circuitry 235 determines, for example, whether or not the deviation determined by the positional relationship acquiring circuitry 2343 exceeds the predetermined threshold.

The predetermined threshold may be set in an arbitrary manner. For example, the predetermined threshold can be set to a small value in order to improve the precision of the fixation.

<User Interface 240>

The user interface 240 includes the display device 241 and the operation device 242. The display device 241 includes the display device 3. The operation device 242 includes various kinds of operation devices and input devices.

The user interface 240 may include, for example, a device, like a touch panel, having the display function and the operation function. In another embodiment, the ophthalmic apparatus may not include at least part of the user interface. For example, the display device may be an external device connected to the ophthalmic apparatus.

<Operation>

Figure 4:
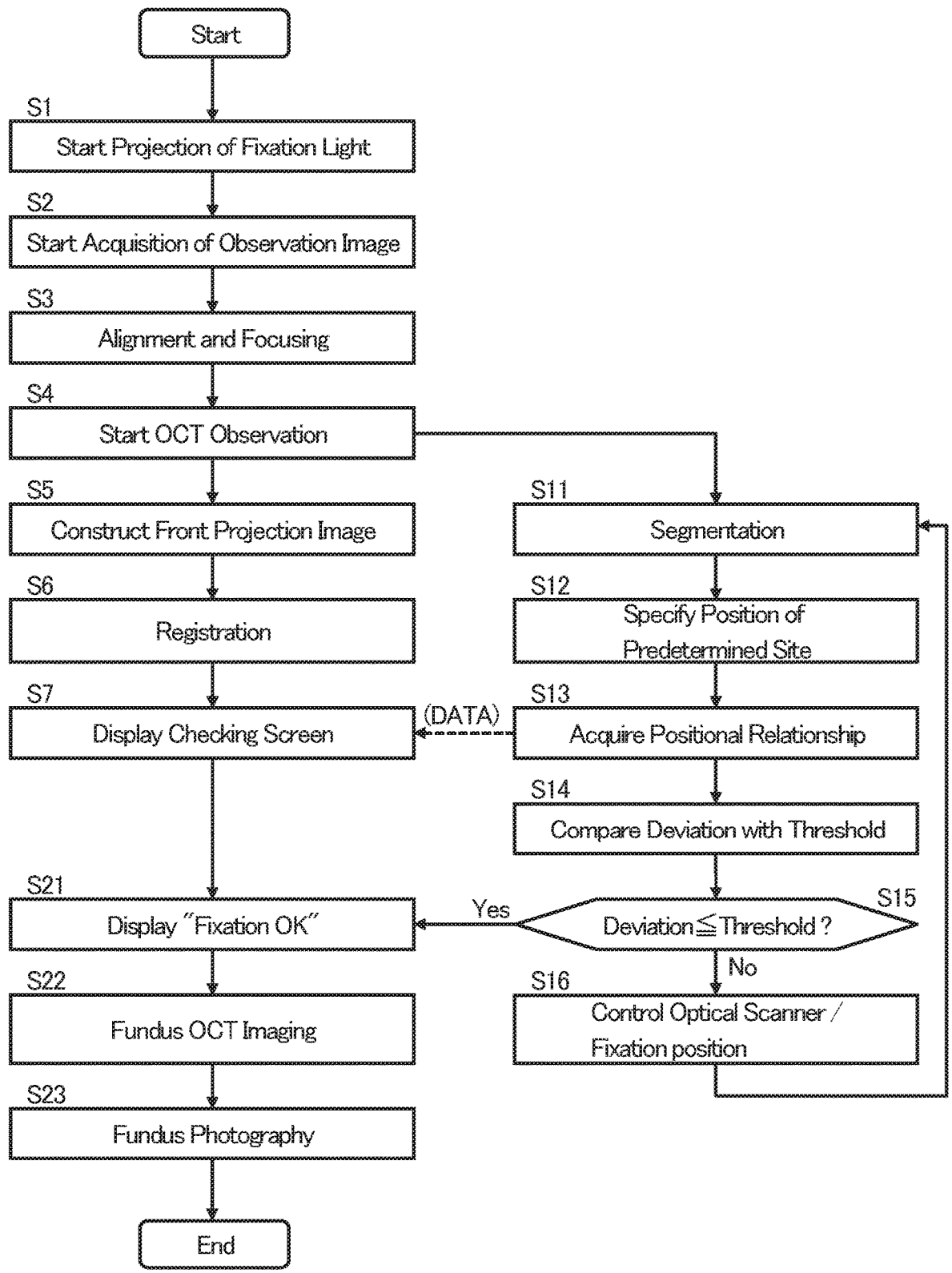
FIG. 4 is a flowchart showing an example of the operation of the ophthalmic apparatus according to the embodiment.

The operation of the ophthalmic apparatus 1 will be described. An example of the operation is shown in FIG. 4.

(S1: Start Projection of Fixation Light)

First, the fixation position is designated. The fixation position designation is performed manually or automatically. In a typical example of manual designation, the main controlling circuitry 211 displays a GUI for fixation position designation on the display device 241. The user uses the GUI and the operation device 242 to set a desired fixation position. In a typical example of automatic designation, the main controlling circuitry 211 designates a fixation position based on information input from the outside. Examples of the information include the electronic medical record of the subject input from the electronic medical record system, and the imaging mode designated manually or automatically. In the present example, it is assumed that "macula" is designated as the fixation position.

The main controlling circuitry 211 controls the LCD 39 to display the fixation target at the position on the screen corresponding to the designated fixation position. Thereby, fixation light is projected onto the subject's eye E. The fixation light is, for example, continuously projected onto the subject's eye E until the completion of imaging.

(S2: Start Acquisition of Observation Image)

The main controlling circuitry 211 controls the illumination optical system 10 and the photographing optical system 30 to start acquisition of an observation image of the subject's eye E. As described above, the observation image is a moving image obtained by photographing the subject's eye E from the front side. At this stage, an observation image of the anterior eye segment is obtained.

The main controlling circuitry 211 displays the observation image on the display device 241 in real time. Further, the main controlling circuitry 211 transfers image frames sequentially obtained as the observation image to the data processing circuitry 230.

In addition, the timing of starting fixation light projection (step S1) and the timing of starting observation image acquisition (step S2) are not limited to the order shown in FIG. 4. For example, the main controlling circuitry executes control to start fixation target projection after the commencement of observation image acquisition. Alternatively, the main controlling circuitry executes control to simultaneously start observation image acquisition and fixation target projection.

(S3: Alignment and Focusing)

Next, the main controlling circuitry 211 controls the alignment optical system 50 to project alignment light onto the subject's eye E, and controls the focus optical system 60 to project focus light onto the subject's eye E.

Further, the main controlling circuitry 211 performs automatic alignment and automatic focusing in the same manner as in a conventional case. Alternatively, the user may perform one or both of manual alignment and manual focusing. Thereby, the alignment and focusing with respect to the fundus Ef are completed.

At a middle stage in step S3, the observation image obtained by the fundus camera unit 2 shifts from an anterior eye segment observation image to a fundus observation image.

(S4: Start OCT Observation)

After completing the alignment and focusing, the main controlling circuitry 211 controls the optical scanner 42 and the OCT unit 100 to start OCT observation. The OCT observation repeats OCT scanning with a predetermined scan pattern at a predetermined repetition rate, to acquire a moving image (a time-series image).

The scan pattern applied to the OCT observation is set automatically or manually. The scan pattern is selected, for example, according to an interested site (e.g., the macula, the optic nerve head, a peripheral area of the fundus). The scan pattern is, typically, a raster scan, a radial scan, a multi-cross scan, a cross scan, a circle scan, a line scan, or the like.

The present example employs a raster scan. Thus, the main controlling circuitry 211 controls to iterate the raster scan. The image constructed based on each of the iterative raster scans is a three dimensional image.

The intervals of the A-lines (i.e., the projection spots of the measurement light LS) in the "raster scan for observation" at this stage may be set wider than those in the "scan for imaging" in step S22 described later. With this, the iteration rate can be increased. In addition, the scan area in the raster scan for observation may be the same as or different from the scan area in the scan for imaging.

Step S4 may include correction of OCT scan conditions. The condition correction includes the optical path length adjustment of the measurement arm or the reference arm, the OCT focus adjustment, the image quality control or the like, as in a conventional case.

After starting the OCT observation, a series of processes shown below is performed in real time and in synchronization with the iteration rate of the raster scans. The OCT unit 100 sends data acquired through each raster scan to the image constructing circuitry 220. The image constructing circuitry 220 constructs a plurality of B-scan images from the data acquired by each raster scan and sends the B-scan images to the controlling circuitry 210. The main controlling circuitry 211 sends the B-scan images corresponding to each raster scan to the data processing circuitry 230. The three dimensional image constructing circuitry 231 constructs a three dimensional image from the B-scan images corresponding to each raster scan, and sends the constructed three dimensional images to each of the image projecting circuitry 232 and the analyzing circuitry 234.

Hereinafter, steps S5 to S6 and steps S11 to S14 (and in some cases steps S15 to S16 as well) are also executed in synchronization with the iteration rate of the raster scans. Further, a series of processes consisting of steps S5 to S7 and a series of processes consisting of steps S11 to S16 are executed in parallel.

(S5: Construct Front Projection Image)

After starting OCT observation, three dimensional images are sequentially input to the image projecting circuitry 232 at timings synchronized with the iteration frequency of the iterative raster scan. The image projecting circuitry 232 constructs front projection images from the three dimensional images sequentially input, and sends the constructed front projection images to the registration processing circuitry 233.

(S6: Registration)

The registration processing circuitry 233 performs registration between the front projection images sequentially input from the image projecting circuitry 232 and the image frames of the observation image transferred by the main controlling circuitry 211.

The combination (or pair) of a front projection image and an image frame to be registered is determined in an arbitrary manner. For example, the registration processing circuitry 233 may be configured to pair the most recently constructed front image and the most recently captured image frame, and apply registration to this pair. To do so, the frame rate (capture rate) of the observation image and the repetition rate of the OCT observation can be synchronized with one another. In another example, the registration processing circuitry 233 may be configured to perform registration between a preset reference image frame and each front projection image.

(S7: Display Checking Screen)

The main controlling circuitry 211 displays a checking screen used for checking the fixation state, on the display device 241. The start timing of displaying the checking screen may be arbitrary. For example, the display of the checking screen can be started at a timing prior to step S1 or at a timing in the period between steps S1 and S6.

Further, the main controlling circuitry 211 displays the observation image whose acquisition has been started in step S2 and the front projection image constructed in step S5, on the checking screen. At this time, the main controlling circuitry 211 displays the observation image and the front projection image using the result of the registration of step S6. That is, since the registration between the image frames constituting the observation image and the front projection images has been performed, the observation image and the front projection images are displayed whose mutual positions are maintained. At this time, one or both of the observation image and the front projection images are displayed as a moving image.

Figure 5:
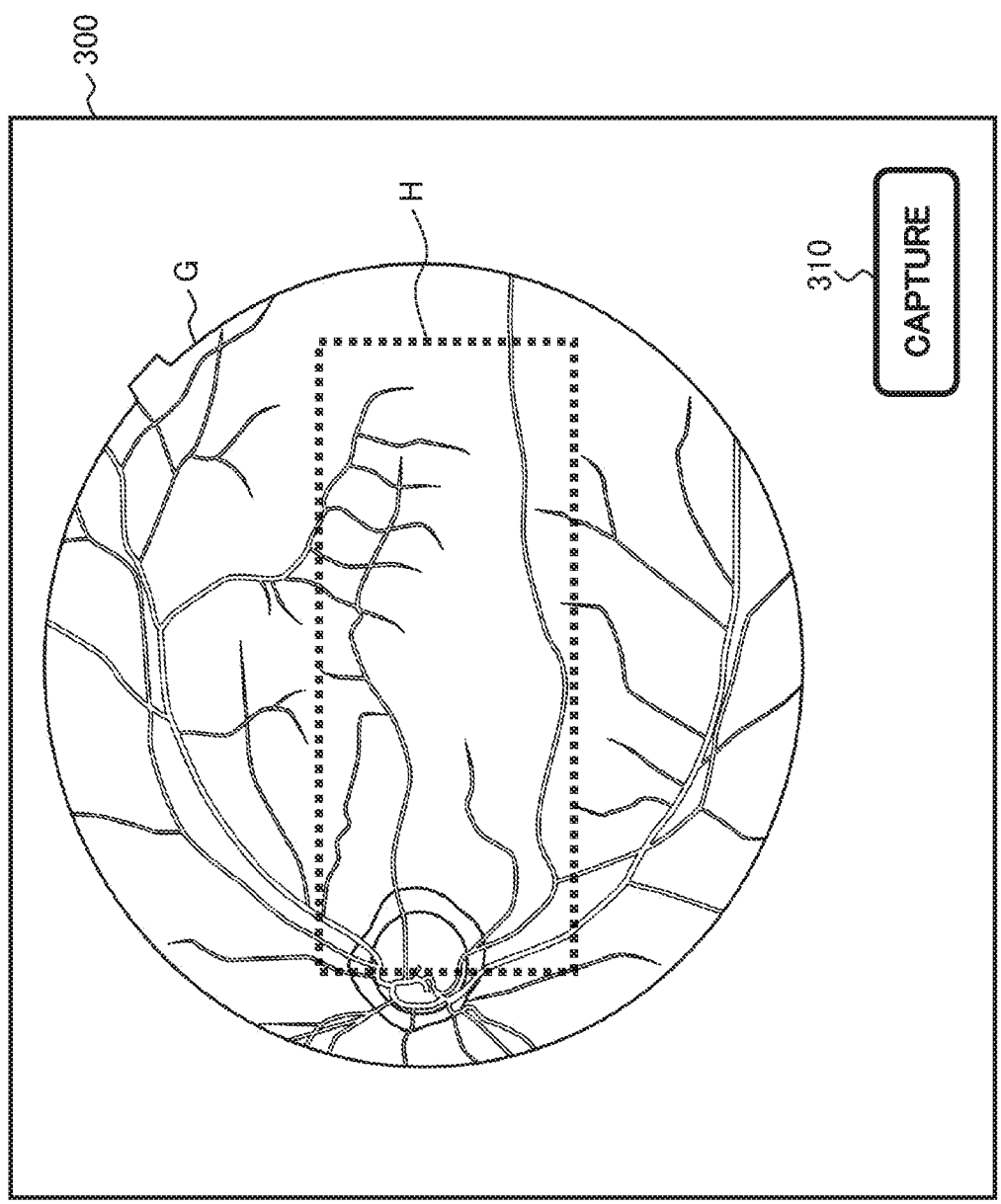
FIG. 5 is a schematic diagram illustrating an example of a screen displayed by the ophthalmic apparatus according to the embodiment.

An example of the checking screen is shown in FIG. 5. On the checking screen 300, the observation image G whose acquisition has been started in step S2 and the front projection image H constructed in step S5 are displayed. Registration of the observation image G and the front projection image H has been carried out in step S6. The present example overlays the front projection image H on the observation image G.

The checking screen 300 is provided with the capture button 310. The capture button 310 is a software key that receives an instruction for performing OCT imaging. In a typical example, the checking screen 300 displays a pointer (not shown in figures). The user can enter an instruction for OCT imaging by clicking the capture button 310 using the operation device 242. When the display device 241 is a touch panel, the user can enter an instruction for OCT imaging by tapping the capture button 310.

(S11: Segmentation)

After starting the OCT observation in step S4, three dimensional images are sequentially input to the segmentation processing circuitry 2341 at timings synchronized with the iteration frequency of the iterative raster scan. The segmentation processing circuitry 2341 analyzes each three dimensional image sequentially input to specify at least one segment. The present example specifies the inner limiting membrane image and the Bruch membrane image. The result of specification obtained by the segmentation processing circuitry 2341 is sent to the position specifying circuitry 2342.

(S12: Specify Position of Predetermined Site)

The position specifying circuitry 2342 specifies the position of the predetermined site of the subject's eye E based on the at least one segment specified by the segmentation processing circuitry 2341. In the present example, the position specifying circuitry 2342 specifies the position where the distance between the inner limiting membrane image and the Bruch membrane image is the shortest. The position specified is assumed to be the macular center position. The result of position specification performed by the position specifying circuitry 2342 is sent to the positional relationship acquiring circuitry 2343.

The result of the position specification performed by the position specifying circuitry 2342 is also sent to the main controlling circuitry 211. The main controlling circuitry 211 displays an image (interested site image) based on the position of the predetermined site (i.e., macular center) specified by the position specifying circuitry 2342, on the checking screen 300. The interested site image is generated by, for example, the data processing circuitry 230 or the main controlling circuitry 211.

The interested site image is displayed, for example, over the front projection image H (and thus over the observation image G). In this case, the position where the interested site image is displayed is determined based on the result of registration.

In a typical example, the three dimensional image used to construct the front projection image H and the three dimensional image analyzed by the position specifying circuitry 2342 are the same. Further, position matching has already been done between the observation image G and the front projection image H through registration. Therefore, the position in the observation image G corresponding to the position specified by the position specifying circuitry 2342 and the position in the front projection image H can be associated with each other by referring to the registration result. Alternatively, the position in the front projection image H corresponding to the position specified by the position specifying circuitry 2342 can be specified by utilizing the fact that the three dimensional image used to construct the front projection image H and the three dimensional image analyzed by the position specifying circuitry 2342 are the same.

Another example will be described. The OCT observation acquires a time-series three dimensional image in synchronization with the iteration rate of the raster scans. Further, the series of processes consisting of steps S5 to S6 and the series of processes consisting of steps S11 to S13 are executed separately from and in parallel with each other. Therefore, it is assumed that there may be a case where, at a certain timing, the three dimensional image that is the origin of the front projection image H displayed on the checking screen 300 is different from the three dimensional image that is the origin of the interested site image displayed together with this front projection image H.

If this is the case, the data processing circuitry 230 can sequentially analyze the image frames of the observation image to detect the time-series displacement of the fundus Ef (e.g., a feature site therein). Alternatively, the position specifying circuitry 2342 can detect the time-series displacement of the fundus Ef from the time-series change in the position of the predetermined site (e.g., the macular center) sequentially specified. The main controlling circuitry 211 or the data processing circuitry 230 can perform registration between two (or more) three dimensional images acquired at different timings based on the time-series displacement of the fundus Ef detected in this way, and registration between the front projection image H displayed on the checking screen 300 and the interested site image displayed together with the front projection image H.

Examples of the interested site image are described. In the first example, the interested site image is an image indicating the position specified by the position specifying circuitry 2342. Such an interested site image may be, for example, a point image displayed at the position in the front projection image H corresponding to the specified position, an arrow image pointing to the specified position, or a like image.

Figure 6:
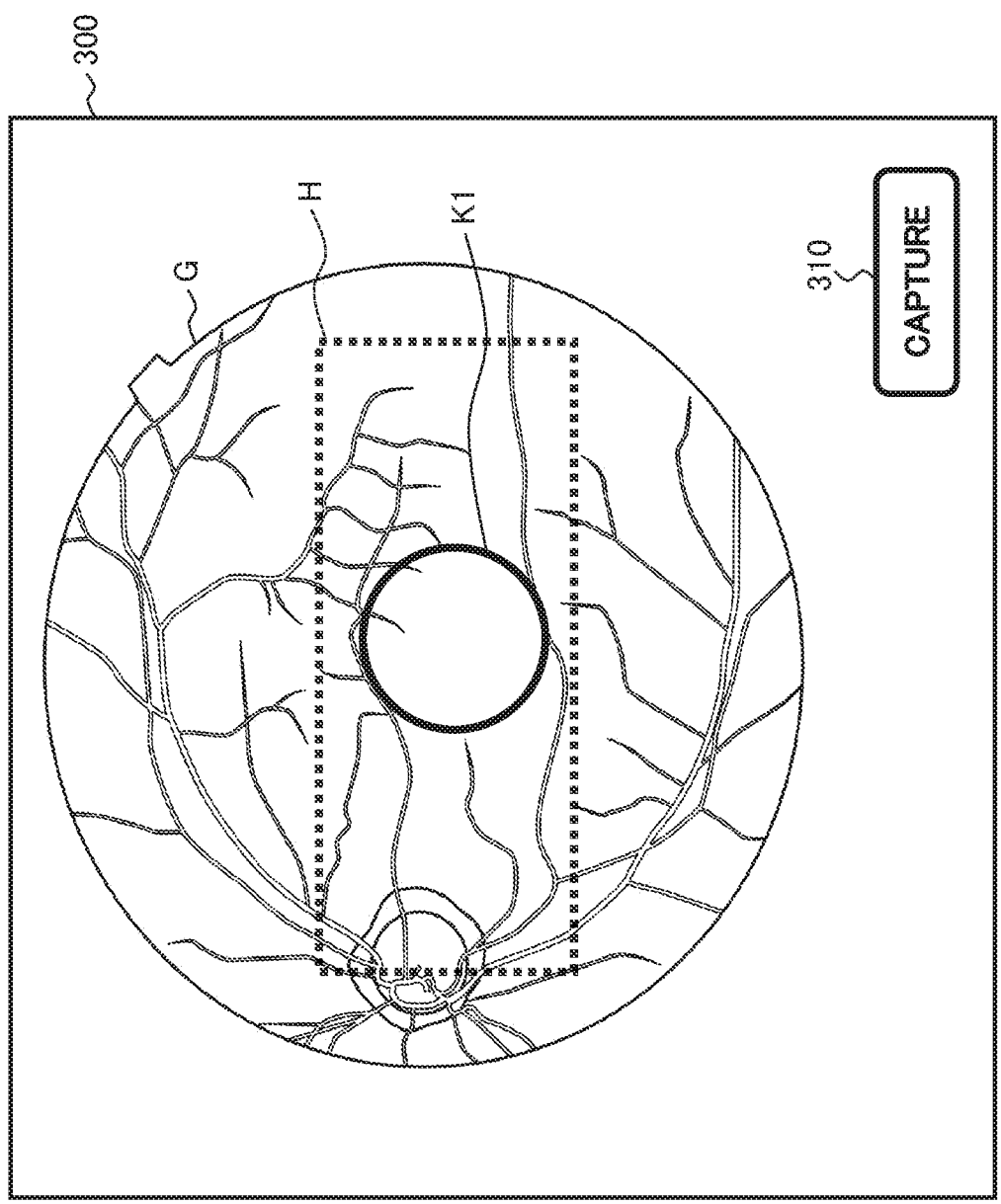
FIG. 6 is a schematic diagram illustrating an example of a screen displayed by the ophthalmic apparatus according to the embodiment.

In the second example, the interested site image is an image indicating the area corresponding to the position specified by the position specifying circuitry 2342. The area is set based on, for example, a site to be specified by the position specifying circuitry 2342, a scan pattern, or the like. As one example, when the position specifying circuitry 2342 has specified the position of the macular center, an interested site image indicating the area of the macula (and its periphery) can be generated. The shape and/or size of the area is determined based on, for example, clinically obtained statistical information, or individual information obtained by analyzing three dimensional images or observation image. The interested site image K1 shown in FIG. 6 is an example of the interested site image.

Further, the main controlling circuitry 211 can display an image (a scan area image) representing the area of the OCT scanning, on the checking screen 300. The scan area image is generated by, for example, the data processing circuitry 230 or the main controlling circuitry 211. The scan area image is displayed, for example, over the front projection image H (and thus over the observation image G).

Figure 7:
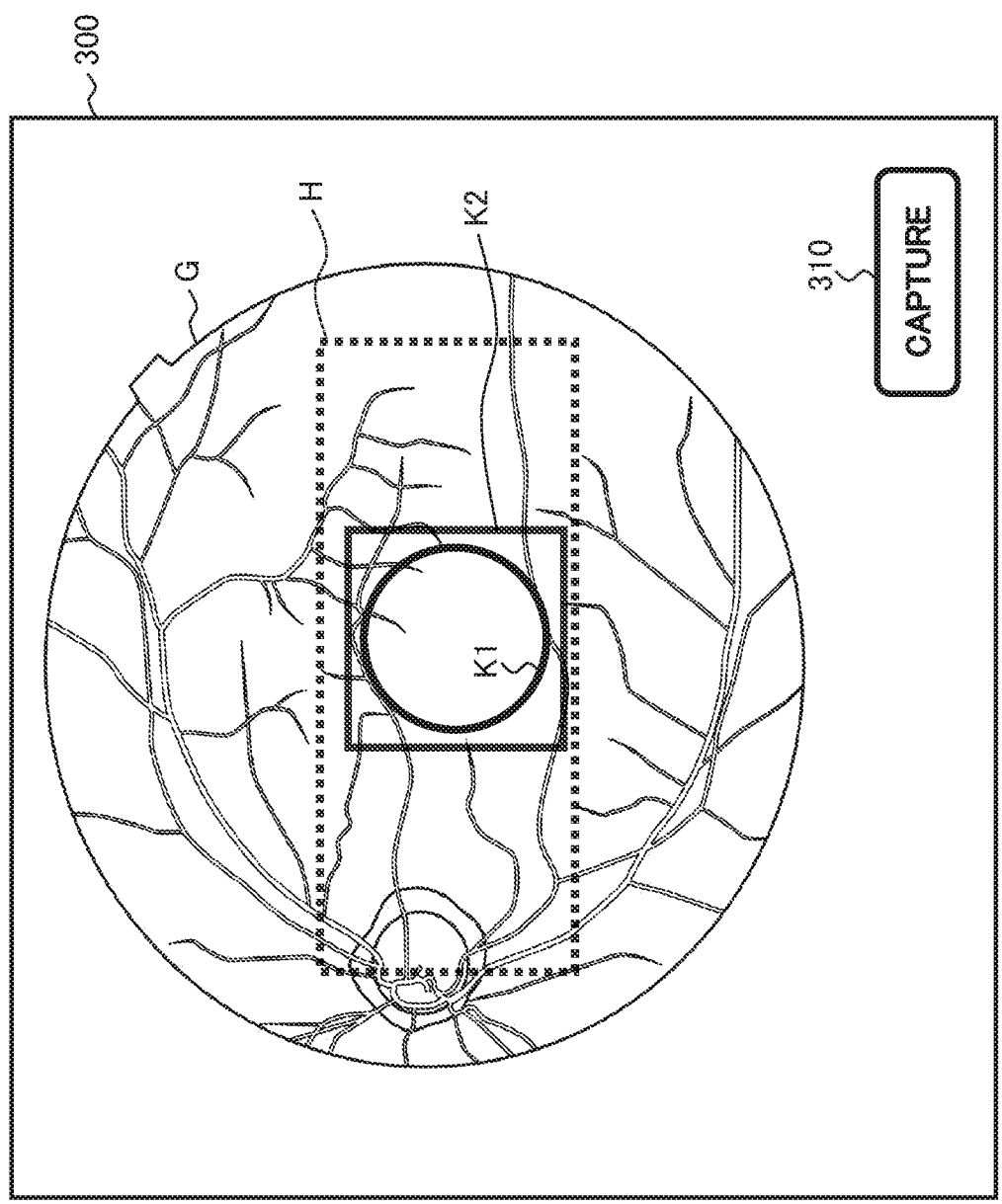
FIG. 7 is a schematic diagram illustrating an example of a screen displayed by the ophthalmic apparatus according to the embodiment.

In the first example, the scan area image indicates the area of the scan pattern (e.g., contour, outer edge) applied in the OCT imaging in step S22. In this case, the scan area image is positioned, for example, such that its center is located at the position corresponding to the position specified by the position specifying circuitry 2342. Alternatively, the scan area image is positioned such that its center is located at the center of the observation image or at the center of the scan area of the OCT observation. The scan area image K2 shown in FIG. 7 is an example of the scan area image.

In the second example, the scan area image indicates the area to be (at least) scanned in the OCT imaging in step S22. The shape and/or size of the area is determined based on, for example, clinically obtained statistical information, or individual information obtained by analyzing three dimensional images or observation image. The scan area image K2 shown in FIG. 7 is an example of the scan area image.

In the third example, the scan area image indicates the area of the scan pattern being applied in the OCT observation. In this case, displayed is a scan area image showing the contour (outer edge) of the front projection image H.

(S13: Acquire Positional Relationship)

The positional relationship acquiring circuitry 2343 determines the positional relationship (deviation vector) between the position of the predetermined site of the subject's eye E specified by the position specifying circuitry 2342 and the area (scan area) of the OCT scanning. Information obtained by the positional relationship acquiring circuitry 2343 (i.e., the deviation such as a deviation vector or its magnitude) is sent to the deviation comparing circuitry 235.

(S14: Compare Deviation with Threshold)

The deviation comparing circuitry 235 compares the deviation acquired by the positional relationship acquiring circuitry 2343 and a predetermined threshold.

(S15: Deviation<Threshold?)

When the deviation comparing circuitry 235 has determined that the deviation exceeds the threshold (deviation>threshold) by the comparison in step S14 (S15: No), the process proceeds to step S16. On the other hand, when the deviation comparing circuitry 235 has determined that the deviation is equal to or less than the threshold (deviation≤threshold) (S15: Yes), the process proceeds to step S21.

(S16: Control Optical Scanner/Fixation Position)

When the deviation comparing circuitry 235 has determined that the deviation exceeds the threshold (deviation>threshold) by the comparison in step S14 (S15: No), the main controlling circuitry 211 controls at least one of the LCD 39 that is displaying the fixation target, and the optical scanner 42 that deflects the measurement light LS.

The control target (the LCD 39 and/or the optical scanner 42) is determined in advance or determined during the processing. In a typical example, the main controlling circuitry 211 may be configured to control one of the LCD 39 and the optical scanner 42 at all times. The determination of the control target may be made, for example, with reference to arbitrary information as the followings: the features and/or attributes of the subject; the features and/or attributes of the subject's eye; the features grasped from the OCT observation image; the features grasped from the observation image; and the features grasped from an examination carried out in the past.

When controlling the LCD 39, for example, the main controlling circuitry 211 changes the display position of the fixation target to cancel out a deviation acquired by the positional relationship acquiring circuitry 2343. In other words, the main controlling circuitry 211 changes the display position of the fixation target so that a deviation acquired by the positional relationship acquiring circuitry 2343 after the control of the LCD 39 becomes zero. Alternatively, the main controlling circuitry 211 may change the display position of the fixation target so that a deviation acquired after the control becomes smaller than the deviation detected in step S13.

When controlling the optical scanner 42, for example, the main controlling circuitry 211 shifts the scan area by the optical scanner 42 to cancel out a deviation acquired by the positional relationship acquiring circuitry 2343. In other words, the main controlling circuitry 211 shifts the scan area so that a deviation acquired by the positional relationship acquiring circuitry 2343 after the control of the optical scanner 42 becomes zero. Alternatively, the main controlling circuitry 211 may shift the scan area so that a deviation acquired after the control becomes smaller than the deviation detected in step S13.

Such control of the LCD 39 and/or the optical scanner 42 regulates the relative position between the subject's eye E (the fundus Ef) and the scan area for the OCT observation. More specifically, when controlling the LCD 39, the relative position is changed by inducing the movement of the fundus Ef. On the other hand, when controlling the optical scanner 42, the relative position is changed by shifting the scan area.

After carrying out the control for the LCD 39 and/or the optical scanner 42, the process returns to step S11. Then, steps S11 to S15 are executed again. When the determination is "No" again in step S15, a routine of steps S11 to S15 is executed again. The routine is repeated until the determination in step S15 becomes "Yes".

In addition, the ophthalmic apparatus can determine that an error occurs when a predetermined period of time passes from a predetermined timing such as the start of examination or the start of OCT observation. Alternatively, the user may determine an error. Such error determination is performed when an appropriate fixation state cannot be achieved easily.

(S21: Display "Fixation OK")

On the other hand, when the deviation is determined to be equal to or less than the threshold (deviation≤threshold) by the comparison in step S14 (S15: Yes), the main controlling circuitry 211 displays information indicating that an appropriate fixation state has been achieved, on the checking screen 300.

The information may be predetermined text (character string) or image. For example, texts such as "fixation OK" or "ready for imaging" can be displayed. In addition, it is possible to display a predetermined image that allows the user to intuitively recognize that an appropriate fixation state has been reached.

In another example, the ophthalmic apparatus 1 may be configured to continue displaying information indicating an inappropriate fixation state during the determination is "No" in step S15, and to switch the display content from the information indicating the inappropriate fixation state to information indicating an appropriate fixation state when the determination has become "Yes" in step S15.

(S22: Fundus OCT Imaging)

The user can perceive from the information displayed in step S21 that the appropriate fixation state has been reached. Alternatively, the user can perceive that the appropriate fixation state has been reached by referring to the observation image G and/or the front projection image H.

Once perceiving that the appropriate fixation state has been reached, the user operates the capture button 310 on the checking screen 300. In response to the operation of the capture button 310, the main controlling circuitry 211 controls the optical scanner 42 and the OCT unit 100 to perform OCT imaging of the fundus Ef. Data acquired by the OCT imaging is used for diagnostic imaging and image analysis.

(S23: Fundus Photography)

For example, after the completion of the fundus OCT imaging, the main controlling circuitry 211 controls the fundus camera unit 2 to perform photographing of the fundus Ef. Typically, color photography using visible light is performed. The fundus image (captured image, photographed image) obtained in step S23 is used for diagnostic imaging and image analysis together with or separately from the data obtained by the OCT imaging. This is the end of the processing according to the present operation example.

<Actions and Effects>

Actions and effects of the ophthalmic apparatus according to some embodiment examples will be described.

The ophthalmic apparatus of some embodiment examples includes a fixation system, a data acquisition device, analyzing circuitry, and controlling circuitry.

The fixation system is configured to project fixation light onto the subject's eye. In the above-described embodiment example, the combination of the LCD 39 and optical elements forming the optical path for guiding the light (fixation light) output from the LCD 39 to the subject's eye E, functions as the fixation system.

The data acquisition device is configured to acquire data by applying OCT scanning to the subject's eye onto which the fixation light is being projected. The OCT scanning is, for example, iteration of a predetermined scan pattern. In the above-described embodiment example, the combination of elements included in the OCT unit 100 and optical elements forming the optical path for guiding the measurement light LS to the subject's eye E, functions as the data acquisition device. The image constructing circuitry 220 and the three dimensional image constructing circuitry 231 also function as part of the data acquisition device.

The analyzing circuitry is configured to analyzes the data acquired by the data acquisition device to specify the position of the predetermined site of the subject's eye. The position specified by the analyzing circuitry is typically a position in the data acquired by the data acquisition device, that is, a position in the area to which the OCT scanning is applied. In the above embodiment example, the analyzing circuitry 234 functions as the analyzing circuitry.

The controlling circuitry is configured to control at least one of the fixation system and the data acquisition device, based on the positional relationship between the position of the predetermined site specified by the analyzing circuitry and the scan area by the data acquisition device. In other words, the controlling circuitry is configured to change the relative position between the subject's eye and the OCT scanning area, based on the positional relationship between the position of the predetermined site specified by the analyzing circuitry and the scan area scanned by the data acquisition device. In the above embodiment example, the main controlling circuitry 211 functions as the controlling circuitry.

In some embodiment examples, the controlling circuitry may be configured to control the data acquisition device to change the scan area based on the positional relationship between the predetermined site of the subject's eye and the scan area. In the above embodiment example, the main controlling circuitry 211 changes the scan area through control of the optical scanner 42.

In some embodiment examples, the controlling circuitry may be configured to control the fixation system to change the fixation position based on the positional relationship between the predetermined site of the subject's eye and the scan area. In the above embodiment example, the main controlling circuitry 211 changes the fixation position through control of the LCD 39.

According to some embodiment examples configured as described above, the relative position between the subject's eye and the scan area can be changed based on the positional relationship between the predetermined area of the subject's eye (e.g., the macular center) and the scan area. Therefore, when fixation loss occurs (that is, when the positional relationship between the predetermined site of the subject's eye and the scan area is not appropriate), the ophthalmic apparatus can regulate the fixation position of the subject's eye and/or the position of the scan area in order to eliminate the fixation loss. As a result, the ophthalmic apparatus can cope with the fixation loss in an appropriate manner.

In some embodiment examples, the data acquisition device may be configured to acquire an image of the subject's eye. In the above embodiment example, the ophthalmic apparatus can construct B-scan images by the image constructing circuitry 220 and construct three dimensional images by the three dimensional image constructing circuitry 231.

Further, the analyzing circuitry may include segmentation processing circuitry, position specifying circuitry, and positional relationship acquiring circuitry.

The segmentation processing circuitry is configured to analyze the image acquired by the data acquisition device to specify at least one segment (e.g., layer structure, layer boundary). In the above embodiment example, the segmentation processing circuitry 2341 functions as the segmentation processing circuitry.

The position specifying circuitry is configured to specify the position of the predetermined site of the subject's eye based on the at least one segment specified by the segmentation processing circuitry. In the above embodiment example, the position specifying circuitry 2342 functions as the position specifying circuitry.

The positional relationship acquiring circuitry is configured to determine the positional relationship between the position of the predetermined site specified by the position specifying circuitry and the scan area by the data acquisition device. In the above embodiment example, the positional relationship acquiring circuitry 2343 functions as the positional relationship acquiring circuitry.

In addition, the controlling circuitry is configured to executes control for at least one of the fixation system and the data acquisition device based on the positional relationship determined by the positional relationship acquiring circuitry.

According to some embodiment examples including the data acquisition device, the analyzing circuitry, and the controlling circuitry configured as described above, the ophthalmic apparatus can determine the position of the predetermined site of the subject's eye with high accuracy and high precision by using OCT images. As a result, the ophthalmic apparatus can regulate the fixation position and the scan area with high accuracy and high precision, thereby eliminating fixation loss in a more appropriate manner.

In some embodiment examples, the segmentation processing circuitry may be configured to specify at least the first segment and the second segment. Further, the position specifying circuitry may be configured to specify the position of the predetermined site of the subject's eye based on a distance distribution between the first segment and the second segment specified by the segmentation processing circuitry.

According to some embodiment examples including the segmentation processing circuitry and the position specifying circuitry configured as described above, the ophthalmic apparatus can appropriately specify the site of the subject's eye that can be specified with referring to the distance between different segments.

The macula (the macular center) is a typical example of the sites that can be specified with referring to the distance between different segments. When specifying the position of the macular center, the following embodiment can be employed.

The data acquisition device is configured to acquire an image of the fundus of the subject's eye. The segmentation processing circuitry is configured to analyze the image of the fundus acquired by the data acquisition device, to specify the image of the inner limiting membrane as the first segment and specify the image of the Bruch membrane as the second segment. Further, the position specifying circuitry can specify, from the distance distribution between the inner limiting membrane image and the Bruch membrane image specified by the segmentation processing circuitry, a position at which the distance is the shortest, and set the specified position as the position of the macular center.

In addition, it is also possible to employ the configuration that specifies the position of the predetermined site through another analysis processing. For example, the position of the predetermined site can be specified based on the position of a predetermined segment. As a typical example thereof, the position of the optic nerve head can be specified by detecting the edge of the segment corresponding to the Bruch membrane. Alternatively, the macula or the optic nerve head can be specified based on the shape of the segment corresponding to the inner limiting membrane. As yet another alternative, OCT angiography can be used to specify the position of blood vessels.

In some embodiment examples, the data acquisition device may be configured to acquire a three dimensional image by scanning a three dimensional region of the subject's eye. Furthermore, the analyzing circuitry may be configured to analyze the three dimensional image acquired by the data acquisition device to specify the position of the predetermined site of the subject's eye. In addition, the ophthalmic apparatus of the embodiment examples may include image projecting circuitry, a photographing device, and registration processing circuitry.

The image projecting circuitry is configured to construct a front projection image from the three dimensional image acquired by the data acquisition device. In the above embodiment example, the image projecting circuitry 232 functions as the image projecting circuitry.

The photographing device is configured to photograph the subject's eye to capture a front image. In the above embodiment example, the combination of the illumination optical system 10 and the imaging optical system 30 functions as the photographing device.

The registration processing circuitry performs registration (position matching) between the front projection image constructed by the image projecting circuitry and the front image acquired by the photographing device. The registration includes at least the process of determining a deviation between the front projection image and the front image. In addition, the registration may further include the process of regulating the positional relationship between the front projection image and the front image so as to cancel out the deviation determined.

In such embodiment examples, the controlling circuitry is configured to display the front image acquired by the photographing device on a display device. Further, the controlling circuitry is configured to display the first image based on the position of the predetermined site of the subject's eye specified by the position specifying circuitry over the front image, based on the result of the registration between the front projection image and the front image. In the above embodiment example, the display device 241 functions as the display device. Further, the interested site image K1 is displayed as an example of the first image.

Further, the controlling circuitry may be configured to display the second image indicating the scan area by the data acquisition device over the front image. In the above embodiment example, the scan area image K2 is displayed as the second image.

In addition, the control circuitry may be configured to display the front projection image over the front image.

According to some embodiment examples including the data acquisition device, the analyzing circuitry, the image projecting circuitry, the photographing device, the registration processing circuitry and the controlling circuitry configured as described above, the ophthalmic apparatus can display the first image indicating the position of the predetermined site of the subject's eye specified from the OCT image, over the front image acquired by using a system (the photographing device) other than OCT. With this, the user can easily grasp the position of the predetermined site of the subject's eye from the display images.

Further, according to such embodiment examples, the ophthalmic apparatus can display the second image indicating the scan area by the data acquisition device, over the front image. With this, the user can easily grasp the area to which OCT scanning has been applied, from the display images. Also, the user can easily grasp the positional relationship between the predetermined site of the subject's eye and the scan area, from the positional relationship between the first image and the second image.

In addition, according to such embodiment examples, the front projection image can be displayed over the front image. Therefore, the user can easily grasp the positional relationship between the front image acquired by the photographing device and the front projection image acquired using OCT scanning. Further, the user can easily grasp the position of the predetermined site in the region of the subject's eye depicted in the front projection image. In addition, the user can easily grasp the positional relationship between the region of the subject's eye depicted in the front projection image and the scan area.

In some embodiment examples, the controlling circuitry may be configured to compare, with a predetermined threshold, a deviation of the scan area from the position of the predetermined site of the subject's eye specified by the position specifying circuitry, and executes control for at least one of the fixation system and the data acquisition device only when the deviation exceeds the predetermined threshold.

According to such embodiment examples, when the deviation of the scan area with respect to the position of the predetermined site of the subject's eye is large, the ophthalmic apparatus can execute control for eliminating the fixation loss. In addition, when the deviation becomes sufficiently small, the ophthalmic apparatus can proceed to an examination (e.g., measurement, imaging).

The embodiments described above are only examples of the present invention. Those who intend to implement the present invention can make any modifications (e.g., omissions, substitutions, replacements, additions) within the scope of the gist of the present invention.

What is claimed is:

1. An ophthalmic apparatus comprising:
a fixation system that projects fixation light onto a subject's eye;
a data acquisition device that acquires time-series data by repetitively applying optical coherence tomography scanning to the subject's eye onto which the fixation light is being projected;
analyzing circuitry that analyzes the time-series data to detect time-series displacement of a predetermined site of the subject's eye in parallel with acquisition of the time-series data by the data acquisition device; and
controlling circuitry that controls at least one of the fixation system and the data acquisition device based on a positional relationship between the time-series displacement and a scan area by the data acquisition device in parallel with the acquisition of the time-series data by the data acquisition device and detection of the time-series displacement by the analyzing circuitry.

2. The ophthalmic apparatus of claim 1, wherein the controlling circuitry controls the data acquisition device to change the scan area based on the positional relationship.

3. The ophthalmic apparatus of claim 1, wherein the controlling circuitry controls the fixation system to change a fixation position based on the positional relationship.

4. The ophthalmic apparatus of claim 1, wherein
the data acquisition device acquires an image of the subject's eye,
the analyzing circuitry includes:
segmentation processing circuitry that analyzes the image to specify at least one segment of the image;
position specifying circuitry that specifies the position of the predetermined site based on the at least one segment; and
positional relationship acquiring circuitry that determines a positional relationship between the position of the predetermined site specified by the position specifying circuitry and the scan area by the data acquisition device, and
the controlling circuitry executes control for at least one of the fixation system and the data acquisition device based on the positional relationship determined by the positional relationship acquiring circuitry.

5. The ophthalmic apparatus of claim 4, wherein
the segmentation processing circuitry specifies at least a first segment and a second segment of the image, and
the position specifying circuitry specifies the position of the predetermined site based on a distance distribution between the first segment and the second segment.

6. The ophthalmic apparatus of claim 5, wherein
the data acquisition device acquires an image of a fundus of the subject's eye,
the segmentation processing circuitry specifies an inner limiting membrane image as the first segment and specifies a Bruch membrane image as the second segment, and the position specifying circuitry specifies a position at which a distance between the inner limiting membrane image and the Bruch membrane image is the shortest as a position of a macular center.

7. The ophthalmic apparatus of claim 1, wherein the data acquisition device acquires a three dimensional image by scanning a three dimensional region of the subject's eye, and the analyzing circuitry analyzes the three dimensional image to specify the position of the predetermined site, the ophthalmic apparatus further comprising:

image projecting circuitry that constructs a front projection image from the three dimensional image;

a photographing device that photographs the subject's eye to acquire a front image; and registration processing circuitry that performs registration between the front projection image and the front image, wherein the controlling circuitry displays the front image on a display device and displays, based on a result of the registration, a first image based on the position of the predetermined site over the front image.

8. The ophthalmic apparatus of claim 7, wherein the controlling circuitry displays a second image indicating the scan area by the data acquisition device over the front image.

9. The ophthalmic apparatus of claim 7, wherein the controlling circuitry displays the front projection image over the front image.

10. The ophthalmic apparatus of claim 1, wherein the controlling circuitry compares a deviation of the scan area with respect to the position of the predetermined site with a predetermined threshold, and executes control for at least one of the fixation system and the data acquisition device only when the deviation exceeds the predetermined threshold.

11. An ophthalmic optical coherence tomography method comprising:

projecting fixation light onto a subject's eye;

acquiring time-series data by repetitively applying optical coherence tomography (OCT) scanning to the subject's eye onto which the fixation light is being projected;

analyzing the time-series data to detect time-series displacement of a predetermined site of the subject's eye, in parallel with acquisition of the time-series data by the data acquisition device; and performing at least one of fixation control and OCT scanning control based on a positional relationship between the time-series displacement and a scan area to which the OCT scanning is applied in parallel with the acquiring the time-series data and the analyzing the time-series data.

* * * * *